United States Patent
Labyed et al.

(10) Patent No.: US 10,376,242 B2
(45) Date of Patent: Aug. 13, 2019

(54) QUANTITATIVE VISCOELASTIC ULTRASOUND IMAGING

(71) Applicant: Siemens Medical Solutions USA, Inc., Malvern, PA (US)

(72) Inventors: Yassin Labyed, Issaquah, WA (US); Liexiang Fan, Sammamish, WA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 1068 days.

(21) Appl. No.: 14/688,965

(22) Filed: Apr. 16, 2015

(65) Prior Publication Data

US 2016/0302769 A1  Oct. 20, 2016

(51) Int. Cl.
*A61B 8/08* (2006.01)
*A61B 8/00* (2006.01)
*G01S 7/52* (2006.01)

(52) U.S. Cl.
CPC .............. *A61B 8/485* (2013.01); *A61B 8/085* (2013.01); *A61B 8/0833* (2013.01); *A61B 8/463* (2013.01); *A61B 8/5223* (2013.01); *G01S 7/52042* (2013.01); *A61B 8/4483* (2013.01)

(58) Field of Classification Search
CPC ....... A61B 8/0825; A61B 8/485; A61B 8/488; A61B 8/463; A61B 8/5223; A61B 8/4483; A61B 8/085; G01S 7/52022; G01S 7/52036; G01S 7/52042
See application file for complete search history.

(56) References Cited

U.S. PATENT DOCUMENTS

| | | | |
|---|---|---|---|
| 5,625,146 A * | 4/1997 | Hull | G01H 13/00 73/574 |
| 8,052,602 B2 * | 11/2011 | Sunagawa | A61B 8/08 600/437 |
| 8,469,891 B2 | 6/2013 | Maleke et al. | |
| 8,961,418 B2 | 2/2015 | Fan | |
| 9,140,781 B2 | 9/2015 | Montaldo et al. | |
| 9,332,962 B2 | 5/2016 | Kim et al. | |
| 2004/0034304 A1 | 2/2004 | Sumi | |
| 2005/0119568 A1 * | 6/2005 | Salcudean | A61B 8/08 600/437 |
| 2009/0005682 A1 | 1/2009 | Fan et al. | |

(Continued)

FOREIGN PATENT DOCUMENTS

| CN | 101699280 A | 4/2010 |
|---|---|---|
| CN | 102078205 A | 6/2011 |

(Continued)

OTHER PUBLICATIONS

Notice of Allowance dated Apr. 19, 2018 in corresponding Korean application No. 2016-0046232.

(Continued)

*Primary Examiner* — Thomas J Hong
*Assistant Examiner* — Helene Bor

(57) ABSTRACT

Viscosity is included in the quantification by an ultrasound imaging system. The log of a spectrum of displacement as a function of time is determined for each of various locations subjected to a shear or other wave. Solving using the log as a function of location provides the complex wavenumber. Various viscoelastic parameters, such as loss modulus and storage modulus, are determined from the complex wavenumber.

15 Claims, 4 Drawing Sheets

(56) References Cited

U.S. PATENT DOCUMENTS

| | | |
|---|---|---|
| 2009/0216119 A1 | 8/2009 | Fan et al. |
| 2010/0160778 A1* | 6/2010 | Eskandari ................ A61B 8/00 600/438 |
| 2010/0191110 A1* | 7/2010 | Insana .................. A61B 8/0825 600/438 |
| 2012/0271166 A1 | 10/2012 | Shao et al. |
| 2013/0237821 A1* | 9/2013 | Amador Carrascal ...................... G01S 7/52042 600/438 |
| 2014/0358447 A1 | 12/2014 | Doyle et al. |

FOREIGN PATENT DOCUMENTS

| | | |
|---|---|---|
| KR | 20120035901 A | 4/2012 |
| KR | 20120102510 A | 9/2012 |
| KR | 20130057435 A | 5/2013 |
| KR | 20140112453 A | 9/2014 |
| WO | WO 2014-055410 | 4/2014 |
| WO | WO 2014128593 A1 | 8/2014 |
| WO | WO 2015009339 A1 | 1/2015 |

OTHER PUBLICATIONS

French Search Report received in Corresponding Application No. FR1653349, dated Mar. 6, 2018.

\* cited by examiner

QUANTITATIVE VISCOELASTIC ULTRASOUND IMAGING

BACKGROUND

The present embodiments relate to ultrasound imaging. In particular, ultrasound viscoelastic imaging is improved.

Several commercial ultrasound systems provide quantitative values or images of tissue stiffness, such as stiffness measured using shear wave imaging. The stiffness is estimated by assuming that the tissue is purely elastic (i.e., assuming that viscosity is negligible). Different approaches are used for measuring stiffness. These different approaches may emphasize different bands of the shear wave frequency spectrum even while assuming that the tissue is purely elastic. For example, some approaches find a peak displacement caused by the shear wave while others find a peak in a derivative of the displacements. The derivative function alters the frequency band being measured. As a result, different ultrasound systems provide different values for the stiffness or shear wave parameter even for the same tissue. Further, human tissue is viscoelastic, so shear wave dispersion is present. Different shear wave frequencies travel at different speeds. The dispersion is governed by the frequency-dependent storage modulus $\mu_1$ and loss modulus $\mu_2$.

BRIEF SUMMARY

By way of introduction, the preferred embodiments described below include methods, instructions, and systems for quantification in viscoelastic ultrasound imaging. Viscosity is included in the quantification by an ultrasound imaging system. The log of a spectrum of displacement as a function of time is determined for each of various locations subjected to a shear or other wave. Solving using the log as a function of location provides the complex wavenumber. Various viscoelastic parameters, such as loss modulus and storage modulus, are determined from the complex wavenumber.

In a first aspect, a method is provided for quantification in viscoelastic ultrasound imaging. An ultrasound system measures displacement over time at first and second locations of tissue within a patient in response to an impulse excitation. A processor applies a Fourier transform in time of the displacement over time for each of the first and second locations. The processor calculates a logarithm of results of the transforming, and solves for a complex wavenumber from the logarithm of the results. A value for a frequency-dependent viscoelastic parameter is determined with the complex wavenumber. The value for the tissue is output to a display.

In a second aspect, a non-transitory computer readable storage medium has stored therein data representing instructions executable by a programmed processor for quantification in viscoelastic ultrasound imaging. The storage medium includes instructions for determining tissue displacements as a function of time in a patient, estimating loss modulus, storage modulus, or both as a function of frequency from the tissue displacements, and outputting the loss modulus, storage modulus or both.

In a third aspect, a system is provided for quantification in viscoelastic ultrasound imaging. A transducer is configured to transmit an acoustic impulse excitation into a patient and configured to scan a region of the patient with ultrasound. A receive beamformer is configured to generate data representing the region at different times after the acoustic impulse excitation. The data is generated from the scan with ultrasound. A processor is configured to estimate tissue displacement induced by the acoustic impulse excitation and to calculate a viscoelastic property of the region amplitude and phase of the tissue displacements from different locations in the region. A display is configured to display an image representing the viscoelastic property.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

In quantitative viscoelastic imaging, the shear wave equation is solved in the frequency domain. The viscoelastic wave equation is given by:

$$\frac{\delta^2 s(t, x, y, z)}{\delta t^2} - \frac{1}{\rho}\left(\mu_1 + \mu_2 \frac{\delta}{\delta t}\right)\nabla^2 s(t, x, y, z) = 0 \quad (1)$$

$$\frac{\delta^2 s(t, x, y, z)}{\delta t^2} - \frac{\mu_1}{\rho}\nabla^2 s(t, x, y, z) = 0 \quad (2)$$

$$vs = \sqrt{\frac{\mu_1}{\rho}} = \sqrt{\frac{E}{3\rho}} \quad (3)$$

where $s(t,x,y,z)$ is the particle displacement (m), $\mu_1$ is the shear modulus (kPa), $\mu_2$ is the shear viscosity (Pa-s), E is the Young's modulus (kPa), vs is the shear wave velocity, and $\rho$ is the density (Kg/m$^3$). The shear modulus has a known relationship with the storage modulus, and the shear viscosity has a known relationship with the loss modulus. Equation 1 assumes that the components of stress are linear functions of the components of strain and their first time derivatives. The second term of equation 1 is a viscosity term, frequently ignored in measuring stiffness with ultrasound.

Equation 1 may be used to estimate any of the viscoelastic parameters. By using the spectrum of the displacements, the viscosity term is not ignored to obtain stable solution. Shear storage modulus, shear loss modulus, shear attenuation, and/or phase velocity are estimated over a bandwidth of the propagating shear wave. Estimates of the viscoelastic parameters may improve the diagnostic capability of ultrasound.

Figure 1:
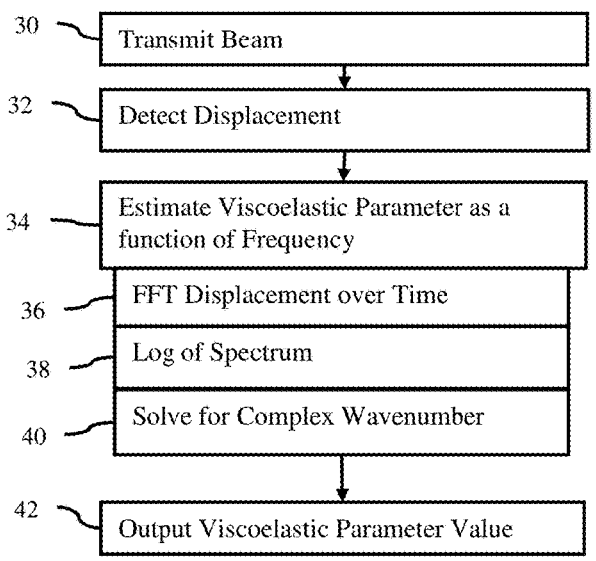
FIG. 1 is a flow chart diagram of one embodiment of a method for quantification in viscoelastic ultrasound imaging.

FIG. 1 shows a method for quantification in viscoelastic ultrasound imaging. The method uses the spectrum of the displacements over time. By taking the log of the spectra from different locations, viscoelastic parameters may be solved as a function of frequency without using a second derivative, which may result in noisy measurements.

Figure 6:
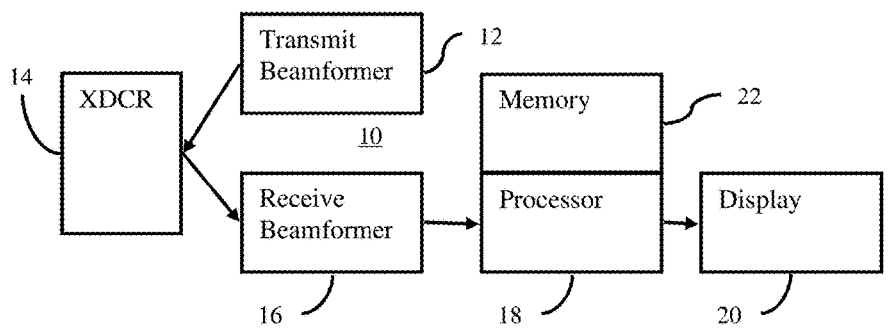
FIG. 6 is a block diagram of one embodiment of a system for quantification in viscoelastic imaging.

The method is implemented by the system of FIG. 6 or a different system. An ultrasound system, such as a system with a transducer and beamformer, performs the transmission and detection acts 30 and 32. A processor of the ultrasound system or a different computer performs the estimation in act 34 and output of act 42 to a display, speaker, or other device. Different components may perform any one or more of the acts.

Additional, different, or fewer acts may be provided. For example, acts 36, 38, and 40 represent one example for estimation, but other acts may be used. In another example, act 30 is not performed and the source of stress is provided by the body, manually, using a thumper, or by other mechanism. Act 42 is optional. The acts are performed in the order described or shown, but may be performed in other orders.

In act 30 of FIG. 1, an acoustic excitation is transmitted into a patient. The acoustic excitation acts as an impulse excitation. For example, a 400 cycle transmit waveform with power or peak amplitude levels similar or higher than B-mode transmissions for imaging tissue is transmitted. In one embodiment, the transmission is a radiation force sequence applied to the field of view. Any acoustic radiation force imaging (ARFI) sequence may be used.

The transmission is configured by power, amplitude, timing or other characteristic to cause stress on tissue sufficient to displace the tissue at one or more locations. For example, a transmit focus is positioned near a bottom, center of the field of view to cause displacement throughout the field of view. The transmission may be repeated for different sub-regions.

The excitation is transmitted from an ultrasound transducer. The excitation is acoustic energy. The acoustic energy is focused, resulting in a three-dimensional beam profile. The excitation is focused using a phased array and/or mechanical focus. The excitation may be unfocused in one dimension, such as the elevation dimension. The excitation is transmitted into tissue of a patient.

In act 32, a displacement profile of response in the patient is determined. For example, the displacement profiles of displacement as a function of time are determined for each of various locations spaced from the shear wave origin, $x_0$ (i.e., shear wave origin at the focus). The excitation causes displacement of the tissue. A shear wave is generated and propagates from the focal region. As the shear wave travels through tissue, the tissue is displaced. Longitudinal waves or other causes of displacement may be used. The tissue is forced to move in the patient.

The displacement caused by the force or stress is measured. The displacement is measured over time at different locations. The displacement measurement may begin before the stress or impulse ends, such as using a different frequency or coding. Alternatively, the displacement measurement begins after the impulse ends. Since the shear wave causing the displacement in tissue spaced from the point or region of stress takes time to travel, the displacement from a relaxed or partially stressed state to a maximum displacement and then to a relaxed state may be measured. Upon ceasing the impulse, the generated shear wave travels from the focus region. As the shear wave passes each location, the displacement rises, peaks, and then falls. Alternatively, the displacement is measured only while the tissue is relaxing.

The measurement is of the amount or magnitude of the displacement. The tissue is moved in any direction. The measurement may be along the direction of greatest movement. The magnitude of the motion vector is determined. Alternatively, the measurement is along a given direction, such as perpendicular to the scan line regardless of whether the tissue is displaced more or less in other directions.

The displacement is detected with ultrasound scanning. A region, such as a region of interest, entire field of view, or sub-region of interest, is scanned with ultrasound. For a given time, ultrasound is transmitted to the tissue or region of interest. Any now known or later developed displacement imaging may be used. For example, pulses with 1-5 cycle durations are used with an intensity of less than 720 $mW/cm^2$. Pulses with other intensities may be used.

Echoes or reflections from the transmission are received. The echoes are beamformed, and the beamformed data represents one or more locations. Multi-beam receive (e.g., receiving along 4, 8, 16, 32, or other number of lines in response to each measurement transmission) may be used. To detect the displacement, ultrasound energy is transmitted to the tissue undergoing displacement and reflections of the energy are received. Any transmission and reception sequence may be used.

By performing the transmitting and receiving multiple times, data representing a one, two, or three-dimensional region at different times is received. The transmission and reception are performed multiple times to determine change due to displacement. By repetitively scanning with ultrasound, the position of tissue at different times is determined.

The echoes are detected using B-mode or Doppler detection. The displacement is detected from the differences for each spatial location. For example, the velocity, variance, shift in intensity pattern (e.g., speckle tracking), or other information is detected from the received data as the displacement.

In one embodiment using B-mode data, the data from different scans is correlated. For example, a current set of data is correlated with a reference set of data. Different relative translations and/or rotations between the two data sets are performed. The location of a sub-set of data centered at a given location in the reference set is identified in the current set.

The reference is a first set of data or data from another scan. The same reference is used for the entire displacement detection or the reference data changes in an ongoing or moving window.

The correlation is one, two or three-dimensional. For example, correlation along a scan line away and toward the transducer is used. For a two-dimensional scan, the translation is along two axes with or without rotation. For three-dimensional scanning, the translation is along three axes with or without rotation about three or fewer axes. The level of similarity or correlation of the data at each of the different offset positions is calculated. The translation and/or rotation with a greatest correlation represents the motion vector or offset for the time associated with the current data being compared to the reference.

Any now known or later developed correlation may be used, such as cross-correlation, pattern matching, or minimum sum of absolute differences. Tissue structure and/or speckle are correlated. Using Doppler detection, a clutter filter passes information associated with moving tissue. The velocity of the tissue is derived from multiple echoes. The velocity is used to determine the displacement towards or away from the transducer. Alternatively, the relative or difference between velocities at different locations may indicate strain or displacement.

The magnitude in distance of the motion vector over time from reference data provides the displacement as a function of time. The period of analysis is over about 10 milliseconds, but may be longer or shorter.

In act 34, one or more viscoelastic parameters are estimated. For example, the loss modulus, storage modulus, or both are estimated. The loss modulus and storage modulus correspond to the viscosity and shear modulus, respectively. In alternative embodiments, the known relationships between storage modulus and shear modulus and/or between loss modulus and viscosity are used to derive one from the others. In yet other embodiments, shear modulus and/or viscosity are estimated instead of storage modulus and loss modulus.

A value for the viscoelastic parameter is estimated for one location. For example, a user selects a location on an ultrasound image. In response, the value for the viscoelastic parameter is output. Values for different locations may be estimated, such as estimating for locations in a region of interest and displaying an image where pixel values are modulated as a function of the values.

The viscoelastic parameter is estimated as a function of frequency from the tissue displacements as a function of time. Rather than using spatial derivatives, the estimation is from log-spectra of the tissue displacements as a function of time for each of the locations. The value for the viscoelastic parameter is determined from the log-spectra across different locations. The estimation uses both phase and amplitude of the tissue displacements for the locations. By analyzing the amplitude and phase information of the displacement spectrum, the complex wavenumber is estimated. The various frequency-dependent viscoelastic parameters may be obtained from the complex wavenumber. This estimation makes use of the full available spectrum of displacement data rather than amplitude only.

Acts 36, 38, and 40 represent one example embodiment for performing the estimation of act 34. In other embodiments, additional, different, or fewer acts are provided. For example, act 36 is performed, but acts 38 and/or 40 are not performed.

In act 36, a processor applies a Fourier transform in time. Any transform to the frequency domain may be used, such as a Fast Fourier transform (FFT). The displacements as a function of time for a given location are transformed. The displacement profile is transformed into a profile as a function of frequency. The processor calculates a spectrum of the displacements over time.

Separate spectra are calculated for separate spatial locations. For each spatial location, the displacements as a function of time are Fourier transformed. The Fourier transform is applied to each location independent of displacements from other locations. The transform provides a set of spectra for a respective set of locations. Any number of locations may be used, such as two or more. In alternative embodiments, a given spectrum is calculated from displacements at more than one location.

The complex wavenumber and resulting viscoelastic parameters may be calculated from the displacements in the frequency domain. For estimating the frequency-dependent viscoelastic parameters, the viscoelastic wave equation in the frequency domain is given by:

$$\frac{\delta^2 S(\omega, x)}{\delta x^2} + h^2 S(\omega, x) = 0 \quad (4)$$

where $S(\omega, x)$ is the spectrum of the displacement $s(t, x)$ at lateral position x, $\omega$ is the angular frequency, and h is the complex wavenumber. The complex wavenumber is given by:

$$h = \left(\frac{\rho \omega^2}{\mu_1(\omega) + i\mu_2(\omega)}\right)^{\frac{1}{2}} \quad (5)$$

where $\rho$ is the density of the tissue, i is the imaginary component, and $\mu_1(\omega)$ and $\mu_2(\omega)$ are the storage modulus and loss modulus, respectively. The density may be assumed or treated as a constant. Any density may be used, such as 1000 kg/m$^3$. Equation (4) is a generalization of Equation (1) in the frequency domain (i.e., the components of stress are linear functions of the components of strain and their first and/or higher order time derivatives). This generalization results in storage and loss moduli that are frequency dependent.

Equation 5 is a second-order differential equation and its solution is given by:

$$S(\omega,x) = S_0(\omega,x_0)e^{ih(\omega)x} = S_0(\omega,x_0)e^{-ik(\omega)x}e^{-\alpha(\omega)x} \quad (6)$$

where $S_0(\omega, x_0)$ is the spectrum of the displacement at lateral position $x_0$ (i.e., origin of the shear wave), $k(\omega)$ is the wavenumber, and $\alpha(\omega)$ is the attenuation coefficient. The parameters $k(\omega)$ and $\alpha(\omega)$ are given by:

$$k(\omega) = -\Re(h(\omega)) \quad (7)$$

$$\alpha(\omega) = \Im(h(\omega)) \quad (8)$$

where $\Re$ is the real part and $\Im$ is the imaginary part of the complex wavenumber.

In act 38, the processor calculates a logarithm of results of the transforming. The logarithm is determined for each spectrum. For each location, the logarithm of the frequency response of the displacements as a function of time is calculated.

Any logarithm may be used. In one embodiment, the natural logarithm is used. To determine the complex wavenumber, the natural logarithm of equation 6 is represented as:

$$\ln(S(\omega,x)) = \ln S_0(\omega,x_0) + ihx \quad (9)$$

Equation 9 defines a line for each frequency as a function of location, x.

In act 40, the processor solves for the complex wavenumber. The logarithm of the spectra as a function of location defines a slope. Solving equation 9 for the complex wavenumber, h, provides:

$$h = -i\frac{\delta \ln(S(\omega, x))}{\delta x}. \quad (10)$$

Any solution finding the slope for a given frequency may be used. The slope between the first and second locations of the logarithm of spectra indicates the complex wavenumber. The slope is of an imaginary component.

In one embodiment, the processor applies a linear least-square fit to the logarithms. The linear least-square fit of the logarithm of the spectra as a function of location indicates the slope or complex wavenumber. In other embodiments, a spatial derivative is used to calculate the complex wavenumber. Other slope determinations may be used.

Returning to act 34, the value for one or more frequency-dependent viscoelastic parameters is estimated from the complex wavenumber. Since the parameters are frequency dependent, values for the parameter at different frequencies are determined or a value for a desired or representative frequency is determined.

Any viscoelastic parameter may be estimated from the complex wavenumber, such as a storage modulus, a loss modulus, a shear modulus, a viscosity, phase velocity (i.e., velocity at a frequency), attenuation, or combinations thereof. Using Equation 5, the processor estimates the frequency-dependent storage modulus and loss modulus as:

$$\mu_1(\omega) = \rho\omega^2 \Re\left(\frac{1}{h^2}\right) \qquad (11)$$

$$\mu_2(\omega) = \rho\omega^2 \Im\left(\frac{1}{h^2}\right) \qquad (12)$$

Using Equations 7 and 8, the processor estimates the frequency-dependent phase velocity and shear wave attenuation as:

$$c(\omega) = \frac{\omega}{k(\omega)} = \frac{-\omega}{\Re(\omega)} \qquad (13)$$

$$\alpha(\omega) = \Im(h) \qquad (14)$$

Other calculations to derive values as a function of frequency for any of the parameters may be used. Equations 11-14 show that the frequency-dependent viscoelastic parameters simply follow from the complex wavenumber, h, calculated in equation 10.

Figure 2:
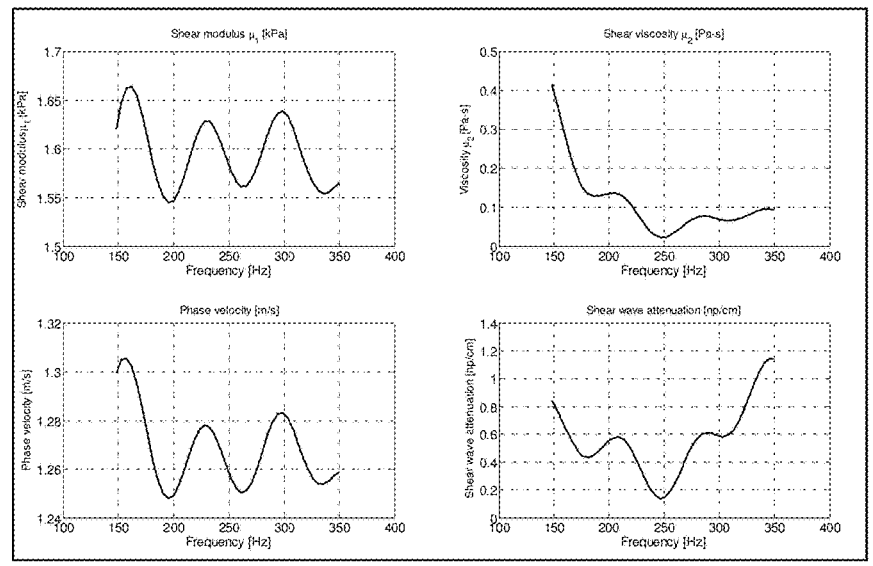
FIG. 2 shows example graphs of viscoelastic parameters in an elastic phantom.
Figure 3:
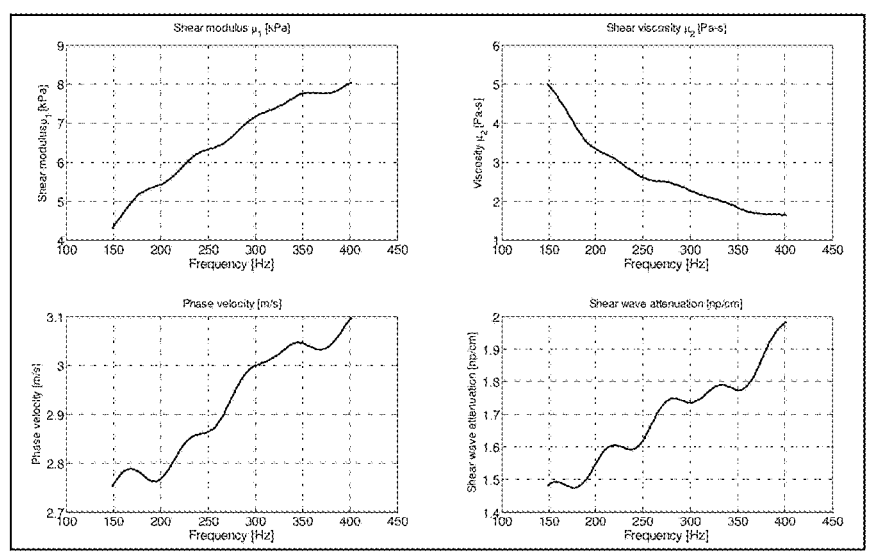
FIG. 3 shows example graphs of viscoelastic parameters in a viscoelastic phantom.
Figure 4:
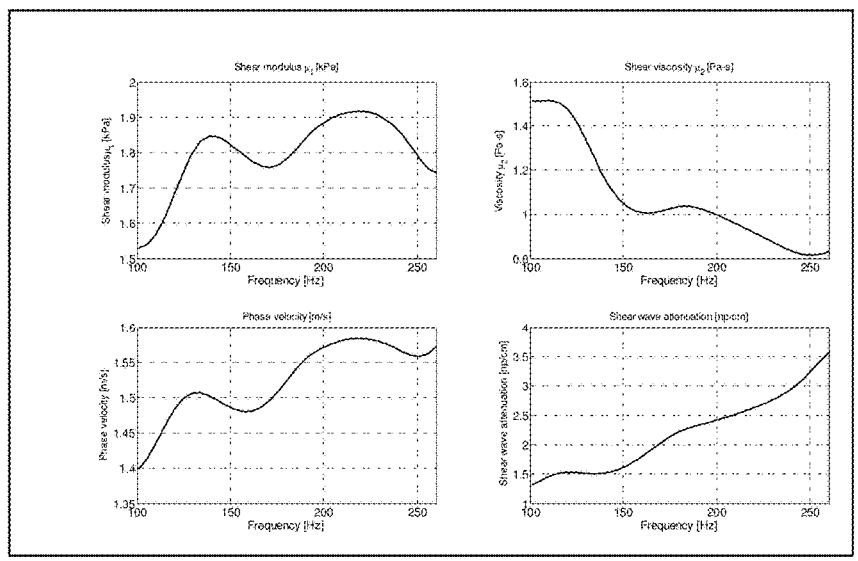
FIG. 4 shows example graphs of viscoelastic parameters in a liver of a patient.

FIGS. 2-4 show examples of estimation of viscoelastic parameters. FIG. 2 shows the parameters calculated from an elastic phantom. FIG. 3 shows the parameters calculated from a viscoelastic phantom. FIG. 4 shows the parameters calculated from a liver of a patient.

FIGS. 2-4 each show an example of the shear modulus (e.g., storage modulus)(equation 11), shear viscosity (e.g., loss modulus)(equation 12), phase velocity (equation 13), and shear wave attenuation (equation 14). The graphs of phase velocity show a phase velocity treating as viscoelastic. The values of the parameters are shown as a function of frequency, which itself may assist in diagnosis.

Group values may be determined. A group value is for the parameter over a range of frequencies. For example, an average over a range of frequencies is calculated. As another example, a derivative over a range of frequencies is calculated. Other functions, such as an integral, difference, variance, or other statistic may be calculated from the values for different frequencies. The viscoelastic parameter at specific frequencies and/or range of frequencies may be determined.

The viscoelastic parameter is determined with both amplitude and phase of the displacements over time. The assumption that the shear modulus and shear viscosity are independent of frequency is not used. A model fitting is not used. The viscoelastic parameter is solved as a function of frequency. A single impulse excitation is all that is needed, so the values are estimated without information responsive to additional impulse excitations. A single ARFI push pulse is sufficient to estimate the viscoelastic parameters as a function of frequency. In alternative embodiments, information responsive to more than one impulse excitation is used for estimating a value of one or more viscoelastic parameters.

The calculation of the value is performed without a spatial derivative (e.g., without a second-order spatial derivative) from the measuring of the displacements to the output of the value. All of the viscoelastic parameters may be calculated without a second-order spatial derivative, resulting in a more stable solution in a low signal-to-noise ratio environment of shear wave imaging. In alternative embodiments, a spatial derivative is used.

In act 42, the value or values are output to the display. The value for the loss modulus, storage modulus, shear modulus, viscosity, phase velocity, attenuation, or combinations thereof are output. The value or values are for a given frequency. Multiple values may be output for a given parameter at different frequencies. A group value, such as a combination of the values for a parameter from different frequencies, may be output.

Figure 5:
FIG. 5 is an example of quantification in viscoelastic ultrasound imaging with quantities determined as a function of frequency.

The output may be text, such as text on or adjacent an ultrasound image. The text may be alphanumeric. FIG. 5 shows an example ultrasound image. In response to the user placing a gate at a location, a graphic of the phase velocity, loss modulus, storage modulus and attenuation as a function of frequency is provided for that gate location. The graphic is a chart or spreadsheet of the viscoelastic parameter values at different frequencies. Additional, different, or less information may be provided.

In another embodiment, a graph or graphs are output. For example, one or more of the graphs shown in FIG. 4 are output. The graphs may cover any range of frequencies, such as frequencies within the bandwidth of the transducer.

In other embodiments, an image is generated from the value or values. For example, a value is calculated for each of a plurality of locations. The solution for the value of a given location is based on spectra in a kernel centered at the location. The kernel defines a spatial (e.g., one-dimensional) window around the location of interest. By adjusting the kernel to other locations, values for the parameter are calculated for different locations. Any one or combination of parameters may be used. Any given frequency or group value may be used. The spatial distribution of the value is mapped to pixel values. The pixels are modulated, at least in part, by the viscoelastic parameter values.

Other outputs may be used. By outputting the value for the tissue of a patient, diagnostically useful information may be output. By measuring displacements with ultrasound, viscoelastic information about the tissue of interest of a patient may be measured and output. The viscoelastic imaging provides more information about tissue mechanical properties than shear wave imaging assuming elastic tissue operation.

The value for the viscoelastic parameter is output alone or with other information. For example, a B-mode image is output as well. A shear velocity and/or other electrography imaging of tissue stiffness may be output with the viscoelastic parameter values.

FIG. 6 shows one embodiment of a system 10 for quantification in viscoelastic ultrasound imaging. The system 10 implements the method of FIG. 1 or other methods. The system 10 includes a transmit beamformer 12, a transducer 14, a receive beamformer 16, an image processor 18, a display 20, and a memory 22. Additional, different or fewer components may be provided. For example, a user input is provided for user interaction with the system. As another example, a separate processor, such as a general or control processor, is provided for deriving displacements and calculating viscoelastic parameters.

The system 10 is a medical diagnostic ultrasound imaging system. In alternative embodiments, the image processor 18, display 20, and/or memory 22 are part of a personal computer, workstation, PACS station, or other arrangement at a same location or distributed over a network for real-time or post acquisition imaging with an ultrasound scanner.

The transmit beamformer 12 is an ultrasound transmitter, memory, pulser, analog circuit, digital circuit, or combinations thereof. The transmit beamformer 12 is configured to generate waveforms for a plurality of channels with different or relative amplitudes, delays, and/or phasing. Upon transmission of acoustic waves from the transducer 14 in response to the generated waveforms, one or more beams are formed. A sequence of transmit beams are generated to scan a two or three-dimensional region. Sector, Vector®, linear, or other scan formats may be used. The same region is scanned multiple times. For flow or Doppler imaging and for shear imaging, a sequence of scans is used. In Doppler imaging, the sequence may include multiple beams along a same scan line before scanning an adjacent scan line. For shear imaging, scan or frame interleaving may be used (i.e., scan the entire region before scanning again). In alternative embodiments, the transmit beamformer 12 generates a plane wave or diverging wave for more rapid scanning.

The same transmit beamformer 12 generates impulse excitations or electrical waveforms for generating acoustic energy to cause displacement. In alternative embodiments, a different transmit beamformer is provided for generating the impulse excitation. The transmit beamformer 12 causes the transducer 14 to generate high intensity focused ultrasound waveforms.

The transducer 14 is an array for generating acoustic energy from electrical waveforms. For an array, relative delays focus the acoustic energy. A given transmit event corresponds to transmission of acoustic energy by different elements at a substantially same time given the delays. The transmit event provides a pulse of ultrasound energy for displacing the tissue. The pulse is an impulse excitation. Impulse excitation includes waveforms with many cycles (e.g., 500 cycles) but that occurs in a relatively short time to cause tissue displacement over a longer time.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. Receive signals are generated in response to ultrasound energy (echoes) impinging on the elements of the transducer 14. The elements connect with channels of the transmit and receive beamformers 12, 16. Alternatively, a single element with a mechanical focus is used.

The receive beamformer 16 includes a plurality of channels with amplifiers, delays, and/or phase rotators, and one or more summers. Each channel connects with one or more transducer elements. The receive beamformer 16 is configured by hardware or software to apply relative delays, phases, and/or apodization to form one or more receive beams in response to each imaging transmission. Receive operation may not occur for echoes from the impulse excitation used to displace tissue. The receive beamformer 16 outputs data representing spatial locations using the receive signals. Relative delays and/or phasing and summation of signals from different elements provide beamformation. In alternative embodiments, the receive beamformer 16 is a processor for generating samples using Fourier or other transforms.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental or other band.

In coordination with the transmit beamformer 12, the receive beamformer 16 generates data representing the region at different times. After the acoustic impulse excitation, the receive beamformer 16 generates beams representing different lines or locations over time. By scanning the region of interest with ultrasound, data (e.g., beamformed samples) is generated.

The receive beamformer 16 outputs beam summed data representing spatial locations. Data for a single location, locations along a line, locations for an area, or locations for a volume are output. Dynamic focusing may be provided. The data may be for different purposes. For example, different scans are performed for B-mode or tissue data than for displacement. Alternatively, the B-mode data is also used to determine displacement. As another example, data for viscoelastic parameter calculation and shear imaging is performed with a series of shared scans, and B-mode or Doppler scanning is performed separately or using some of the same data.

The image processor 18 is a B-mode detector, Doppler detector, pulsed wave Doppler detector, correlation processor, Fourier transform processor, application specific integrated circuit, general processor, control processor, image processor, field programmable gate array, digital signal processor, analog circuit, digital circuit, combinations thereof or other now known or later developed device for detecting and processing information for display from beamformed ultrasound samples. In one embodiment, the processor 18 includes one or more detectors and a separate processor. The separate processor is a control processor, general processor, digital signal processor, application specific integrated circuit, field programmable gate array, network, server, group of processors, data path, combinations thereof or other now known or later developed device for determining displacements and calculating viscoelastic properties. For example, the separate processor is configured by hardware and/or software to perform any combination of one or more of the acts 34-42 shown in FIG. 1.

The processor 18 is configured to estimate tissue displacement induced by the acoustic impulse excitation. Using correlation, tracking, motion detection, or other displacement measuring, the amount of shift in position of the tissue is estimated. The estimation is performed multiple times through a period, such as from prior to the tissue moving due to the impulse to after the tissue has mostly or completely returned to a relaxed state (e.g., recovered from the stress caused by the impulse excitation). The processor 18 estimates tissue displacement as a function of time for each of a plurality of locations.

The processor 18 is configured to calculate a viscoelastic property. The amplitude and phase of the tissue displacements from different locations in the region are used. By calculating log-spectra of the tissue displacements over time for the locations, the processor 18 determines the complex wavenumber. The value or values for one or more viscoelastic parameters are calculated from the complex wavenumber. The complex wavenumber represents the shear wave as a function of frequency, allowing determination of the viscoelastic parameters as a function of frequency.

The processor 18 operates pursuant to instructions stored in the memory 22 or another memory for quantification in viscoelastic ultrasound imaging. The memory 22 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 20 is a CRT, LCD, projector, plasma, or other display for displaying two-dimensional images or three-dimensional representations. The display 20 is configured by the processor 18 or other device by input of the signals to be displayed as an image. The display 20 displays an image representing the viscoelastic property for one or more locations. The image represents the viscoelastic property in any manner, such as test, graph, or modulation of pixels in a region of interest or an entire image.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for quantification in viscoelastic ultrasound imaging, the method comprising:
   measuring, with an ultrasound system, displacement over time at a first location of tissue within a patient in response to an impulse excitation;
   measuring, with the ultrasound system, displacement over time at a second location of the tissue within the patient in response to the impulse excitation;
   Fourier transforming, by a processor, in time the displacement over time for each of the first and second locations;
   calculating, by the processor, a logarithm of results of the transforming of the displacement over time;
   solving, by the processor, for a complex wavenumber from the logarithm of the results;
   determining a value for a frequency-dependent viscoelastic parameter with the complex wavenumber; and
   outputting, to a display, the value for the tissue.

2. The method of claim 1 further comprising:
   transmitting the impulse excitation into the patient, the impulse excitation comprising an acoustic excitation;
   wherein measuring the displacements comprises repetitively scanning the first and second locations with ultrasound.

3. The method of claim 1 wherein measuring the displacements at the first and second locations comprises transmitting ultrasound to the tissue and receiving reflections from the transmitting, the transmitting of the ultrasound and receiving being performed multiple times, and detecting the displacement from the reflections from the multiple receiving.

4. The method of claim 1 wherein measuring comprises measuring the displacements at the first and second locations caused by a shear wave resulting from the impulse excitation.

5. The method of claim 1 wherein measuring the displacements over time at the first and second locations comprises measuring the displacements after the impulse excitation.

6. The method of claim 1 wherein Fourier transforming comprises generating spectra of the displacements over time for each of the first and second locations.

7. The method of claim 1 wherein calculating the logarithm comprises calculating a natural logarithm of spectra as the results.

8. The method of claim 1 wherein solving comprises applying a linear least-square fit to the logarithm.

9. The method of claim 1 wherein solving comprises determining a slope between the first and second locations of the logarithm of spectra as the results, the complex wavenumber comprising the slope of an imaginary component.

10. The method of claim 1 wherein determining the value comprises determining a storage modulus, a loss modulus, a shear modulus, a viscosity, or combinations thereof.

11. The method of claim 1 wherein determining the value for the frequency-dependent viscoelastic parameter comprises determining as a function of a range of different frequencies.

12. The method of claim 1 wherein determining comprises determining with both amplitude and phase of the displacements over time.

13. The method of claim 1 wherein determining comprises determining without a spatial derivative from measuring the displacements to the determining of the value.

14. The method of claim 1 wherein determining comprises determining in response to the single impulse excitation without information from another impulse excitation.

15. The method of claim 1 wherein outputting comprises mapping the value to a pixel or outputting the value as text.

* * * * *